(12) United States Patent
Grolman et al.

(10) Patent No.: US 9,850,348 B2
(45) Date of Patent: Dec. 26, 2017

(54) PROCESS FOR THE PREPARATION OF A POLYAMIDE

(71) Applicant: DSM IP ASSETS B.V., Heerlen (NL)

(72) Inventors: Eric Grolman, Echt (NL); Rudy Rulkens, Echt (NL); Konraad Albert Louise Hector Dullaert, Echt (NL); Renier Henricus Maria Kierkels, Echt (NL); Geert Adelina Rudolf Vanden Poel, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/763,642

(22) PCT Filed: Jan. 30, 2014

(86) PCT No.: PCT/EP2014/051804
§ 371 (c)(1),
(2) Date: Jul. 27, 2015

(87) PCT Pub. No.: WO2014/118278
PCT Pub. Date: Aug. 7, 2014

(65) Prior Publication Data
US 2015/0361216 A1    Dec. 17, 2015

(30) Foreign Application Priority Data
Jan. 30, 2013    (WO) ............... PCT/EP2013/051811

(51) Int. Cl.
| C08G 69/30 | (2006.01) |
| C08G 69/32 | (2006.01) |
| C07C 209/68 | (2006.01) |
| C07C 51/41 | (2006.01) |
| C08G 69/26 | (2006.01) |
| C08L 77/06 | (2006.01) |
| C08L 77/10 | (2006.01) |

(52) U.S. Cl.
CPC ............ *C08G 69/32* (2013.01); *C07C 51/412* (2013.01); *C07C 209/68* (2013.01); *C08G 69/26* (2013.01); *C08G 69/265* (2013.01); *C08G 69/30* (2013.01); *C08L 77/06* (2013.01); *C08L 77/10* (2013.01)

(58) Field of Classification Search
CPC ......... C08L 77/06; C08L 77/10; C08G 69/26; C08G 69/265
See application file for complete search history.

(56) References Cited

U.S. PATENT DOCUMENTS

| 3,379,696 | A | * | 4/1968 | Wiloth | .................. C08G 69/30 526/59 |
| 5,128,442 | A | | 7/1992 | Pipper et al. | |
| 2002/0183479 | A1 | * | 12/2002 | Rulkens | ................. C08G 69/26 528/310 |
| 2013/0172521 | A1 | * | 7/2013 | Nakai | .................... C08G 69/26 528/347 |

FOREIGN PATENT DOCUMENTS

| WO | WO 01/25311 | 4/2001 |
| WO | WO 2007/085406 | 8/2007 |
| WO | WO 2012/070457 | 5/2012 |

OTHER PUBLICATIONS

International Search Report for PCT/EP2014/051804 dated Mar. 3, 2014, 5 pages.

* cited by examiner

*Primary Examiner* — Gregory Listvoyb
(74) *Attorney, Agent, or Firm* — Nixon & Vanderhye P.C.

(57) ABSTRACT

The invention relates to a process for preparing a semi-aromatic polyamide from diamine and dicarboxylic acid, comprising steps of •(i) dosing a liquid diamine to an agitated powder comprising an aromatic dicarboxylic acid thereby forming a powder comprising a diamine/dicarboxylic acid salt (DD-salt), and •(ii) solid-state polymerizing the DD-salt to obtain the polyamide.

15 Claims, 1 Drawing Sheet

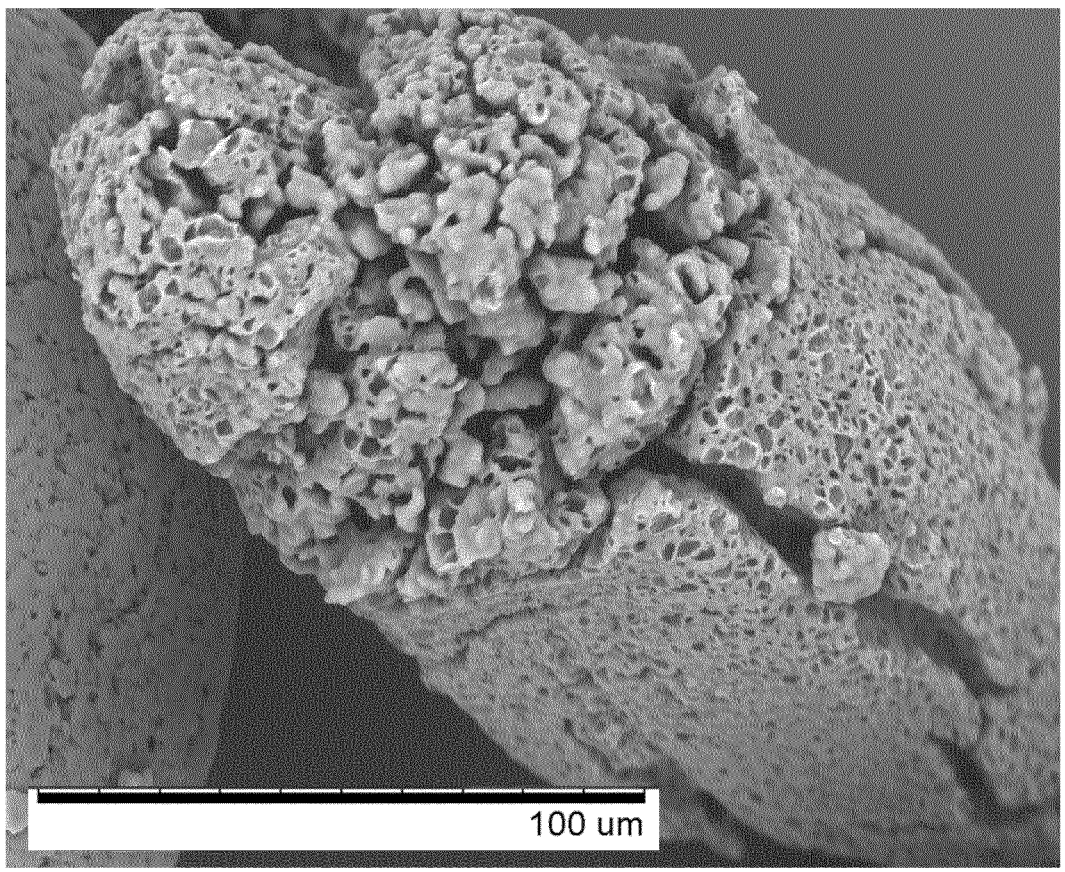

PROCESS FOR THE PREPARATION OF A POLYAMIDE

This application is the U.S. national phase of International Application No. PCT/EP2014/051804 filed 30 Jan. 2014 which designated the U.S. and claims priority to PCT/EP2013/051811 filed 30 Jan. 2013, the entire contents of each of which are hereby incorporated by reference.

The invention relates to a process for preparing polyamides made from diamine and dicarboxylic acid, so called AA-BB polyamides, and more particular to a process for preparing semi-crystalline semi-aromatic AA-BB polyamides. The invention also relates to products obtainable by said process.

There are various ways to produce a polyamide. The known processes include melt polymerization, solution polymerization, suspension polymerization, and solid-state polymerization, and combinations thereof. Polyamides prepared from diamine and dicarboxylic acid are often manufactured by condensing appropriate salts of the diamine and dicarboxylic acid in the molten state. Such a procedure, however, is less suitable for the more heat-sensitive and high melting polyamides, as this generally leads to side reactions resulting in degradation of the polymers. Therefore there is an interest in low temperature processes for their preparation, such as solid-state polymerization, which is abbreviated herein as SSP.

Well-known and widely applied processes for the preparation of polyamides are multi-step processes comprising SSP as a further step. Examples thereof include processes wherein in a first step a prepolymer is made in aqueous solution, in suspension in an inert liquid, or in a melt. The prepolymer so formed is isolated from the solution or suspension, and solidified, or directly solidified from the melt, and further polymerized to a higher molecular weight polymer while in solid-state. Such a process comprising further polymerization of a prepolymer in the solid-state is also known as solid-state post-condensation process or solid-state finishing, and is abbreviated herein as Post-SSP.

For AA-BB polyamides also solid-state polymerization processes are known wherein salts of diamine and dicarboxylic acid are polymerized directly to a polyamide polymer of desired molecular weight, in the solid state, for example in the form of a powder. Such salt powder solid-state polymerization is also referred to as direct solid-state polymerization, which is herein abbreviated as Direct-SSP.

Solid-state polymerization processes, for polyamides, both Post-SSP and the Direct-SSP are also described in the book on "Solid-state Polymerization" by. C. D. Papaspyrides and S. N. Vouyiouka, Wiley, 2009.

A problem for low temperature processes are long reaction times, which is typically solved by using a catalyst to rate up the condensation reaction. Long reaction times are also an issue in melt polymerization, wherein often phosphorous-containing catalysts are being used. The need of addition of catalysts in solid-state polymerization processes was also recognized early on. According to R. Pfaender in the book on "Solid-state Polymerization" by. C. D. Papaspyrides and S. N. Vouyiouka, Wiley, 2009, page 167, the reaction rate of the solid process is not high enough and is significantly lower than for comparable melt or solvent processes. The problem of reactivity is known to be even more emphasized with aromatic dicarboxylic acids, such as terephthalic acid and isophthalic acid, which are known to be less reactive than aliphatic dicarboxylic acids, such as adipic acid, as reported e.g. in the study of "The condensation Kinetics of Polyphthalamides: I. Diamines and Diacids of Dimethylesters" done by Malluche J.; Hellmann, G. P.; Hewel M.; Liedloff, H. J.; Polym. Eng. Sci. 2007, 47, 1589.

Examples of patents about Post-SSP and Direct-SPP processes for polyamides are the following.

JP-62020527-A2 describes a process for the preparation of polyamide-6T, starting from an equimolar salt of 1,6-hexanediamine and terephthalic acid (abbreviated herein as 6T salt). The salt was prepared from an aqueous solution, from which it was separated as a solid powder. The polymerization process comprised a suspension polymerization step followed by a Post-SSP step. First a prepolymer was prepared in a suspension of the salt in cresol, with nitrogen bubbling through, at elevated temperature, but such that the salt was not molten. Then the prepolymer was isolated, and a further polymerization was carried out in the presence of sodium hypophosphite as catalyst, in a nitrogen atmosphere. Without the sodium hypophosphite catalyst the polymerization took a much longer time and a gelled material was obtained.

U.S. Pat. No. 4,925,914 describes a suspension polymerization process wherein a salt of a diamine and dicarboxylic acid was dispersed in an inert liquid together with a phosphorous containing catalyst and polymerized while being in suspension, and then the polymer was isolated from the reaction medium and analysed. The salt and the catalyst had to be finely dispersed in the reaction medium, by intensive mixing with the use of a high shear mixer. The examples included various semi-aromatic homopolymers. Typical values for the yield of the resulting polymer were in the range of 23% to 76%.

U.S. Pat. No. 5,128,442 describes a Direct-SSP process starting from a solid salt of a diamine and a dicarboxylic acid. In the process of U.S. Pat. No. 5,128,442 the solid salt is prepared from a solution, suspension or dispersion comprising the dicarboxylic acid and the diamine and a catalytically effective phosphorous compound evenly distributed therein. The salt is polymerised in the solid-state at a first reaction temperature to form a prepolymer. The prepolymer is further polymerized at a second, higher reaction temperature to a higher molecular weight polymer. In one example a semi-aromatic polyamide, PA-6T/66 (50/50 mole/mole), with a melting temperature of 302° C. was prepared from a 6T/66 salt, obtained from an aqueous solution in the presence of a catalyst. The polymerization took 33 hours and the resulting polymer had a total number of end-groups of 360 to 380 millimolar equivalents per kg (meq/kg), corresponding to a molecular weight of only about 3,000 g/mol. The reaction time is considered still rather long, in view of the presence of the catalyst and even resulting in a polymer with a lower molecular weight. It is further believed that the use of higher reaction temperatures in the method of this patent is problematic and effectively limited by severe sticking of solid material.

The salt preparation is typically done in a solvent or diluent. The salt may be first polymerized in the solvent or diluent by solution or suspension polymerization into a prepolymer, then isolated as a solid prepolymer and then subjected to Post SSP to form the end-polymer. Alternatively, the salt is first isolated from the solvent or diluent as a solid powder, and polymerized by melt polymerization or solid state polymerization. Alternative methods for salt preparation are described in U.S. Pat. No. 5,801,278 and U.S. Pat. No. 5,874,520 in which cryogenic media are used. U.S. Pat. No. 5,874,520 describes a process in which solid diamine carbamates are mixed with solid dicarboxylic acids. These compounds are in particular mixed under high shear conditions, which is to reveal "fresh" particle surfaces having unreacted molecules by frictional rubbing or the like. Cryogenic media (e.g. dry ice or nitrogen) are used, not only to control the heat of the reaction, but also to maintain the reaction mixture in solid state. U.S. Pat. No. 5,801,278 describes the preparation of diamine/dicarboxylic acid salts, in the presence of a cryogenic medium, such as dry ice and liquid nitrogen. U.S. Pat. No. 5,801,278 further illustrates that the same process carried out without a cryogenic medium results in the formation of a paste rather than a free-flowing powder. Use of organic solvents, as in suspension polymerization, or cryogenic media complicates the overall process and leads to extra costs which is not desired or even prohibits large scale production. Semi-crystalline semi-aromatic polyamides are high performance thermoplastics, which have a high price, in part due to their production costs. Thus there is a need to optimize processes for the production of the semi-crystalline semi-aromatic AA-BB polyamides, allowing production in an efficient manner without gelation in a high yield.

An aim of the invention is an optimized process for preparing semi-crystalline semi-aromatic polyamides. This aim have been achieved by the process according to the invention, comprising steps of
  (i) dosing a liquid diamine to an agitated powder comprising an aromatic dicarboxylic acid thereby forming a powder comprising a diamine/dicarboxylic acid salt, and
  (ii) solid-state polymerizing the said diamine/dicarboxylic acid salt to obtain the polyamide.

A direct result of the process according to the invention is that all steps are done in the solid state, thus without melting, or dissolving or dispersing in a liquid, or cooling with a cryogenic medium. Use of solvents, dispersing agents, cryogenic media, and handling and recycling thereof can be omitted, thereby saving on handling and energy costs. The semi-crystalline semi-aromatic polyamide produced with the process according to the invention does not show signs of gelation and is obtained in high yield.

Polyamides made from diamine and dicarboxylic acid are also known as AA-BB polyamides. The nomenclature is adhered to as used in Nylon Plastics Handbook, Edited by Melvin I. Kohan, Hanser Publishers, 1995; e.g. PA-6T denotes a homopolymer with building blocks 1,6-hexanediamine and terephthalic acid, PA-66/6T denotes a copolymer made from 1,6-hexanediamine, adipic acid and terephthalic acid and a blend of PA-66 and PA-6T is described as PA-66/PA-6T.

The term "polyamide" as used herein includes both homopolyamides and copolyamides, unless specifically expressed otherwise. The process according to the invention allows for the production of a copolyamide, or polyamide copolymer, when more than one diamine and/or more than one dicarboxylic acid are used, whereas a homopolyamide, or polyamide homopolymer, is produced when only one diamine and one dicarboxylic acid are used. Homopolyamides and copolyamides are herein together also referred to as (co)polyamide.

With the terms "diamine" and "dicarboxylic acid" in the wording "the semi-aromatic (co) polyamide is prepared from diamine and dicarboxylic acid" is also meant to include diamine comprising two or more different diamines, as well as dicarboxylic acid comprising two or more different dicarboxylic acids, unless explicitly or implicitly indicated otherwise. For example for homopolyamides only one diamine and only one dicarboxylic acid is used.

The polyamide obtained with the process is a semi-aromatic polyamide. With the term semi-aromatic is herein understood that the polyamide comprises repeat units comprising aromatic groups, next to other repeat units, in particular aliphatic repeat units. More particular, the semi-aromatic polyamide obtained by the process comprises repeat units derived from aromatic dicarboxylic acid. Aromatic dicarboxylic acids are dicarboxylic acids wherein the carboxylic acid groups (—CO2H groups) are directly connected to the aromatic unit without methylene or other aliphatic units in between.

With the term diamine/dicarboxylic acid salt is herein understood a diammonium dicarboxylate salt obtained from contacting a dicarboxylic acid and a diamine and resulting from the neutralisation reaction between the dicarboxylic acid and the diamine. The term "diamine/dicarboxylic acid salt" is herein also abbreviated herein as DD-salt.

In the process according to the invention a diamine/dicarboxylic acid salt is formed by dosing a diamine to an agitated powder comprising an aromatic dicarboxylic acid. This step is herein referred to as salt-preparation step, or step (i).

With the term "agitated powder" is herein meant that powder particles are kept in motion. This can be accomplished, for example, mechanically, or by gas flow, or by gravity, or by any combination thereof, like in agitation by stirring, tumbling in rotating vessels, or by fluidization in a fluidized bed reactor. The resulting DD-salt is typically in the form of a powder.

A powder is herein understood to be granular material consisting of discrete and substantially solid particles. These particles, referred to as powder particles, suitably have a particle size of from sub-micron to about 2 mm or less.

The dicarboxylic acid used in the salt-preparation step (i) is in the form of a powder. The use of a dicarboxylic acid powder in the salt-preparation step (i) implies that the agitated powder has a temperature below the melting temperature of the dicarboxylic acid. The preparation of the DD-salt in an agitated powder also implies that the temperature of the powder is below the melting temperature of the DD-salt (further referred herein as "Tm-salt").

The temperature of the agitated powder during the dosing of the diamine is herein referred to with the term "powder temperature". The temperature of the agitated powder can be measured by standard means, for example with a thermocouple.

The agitated powder comprises at least one aromatic dicarboxylic acid. The agitated powder in step (i) may comprise a mixture of two or more dicarboxylic acids, for example two or more aromatic dicarboxylic acids, or an aromatic dicarboxylic acid and an aliphatic dicarboxylic acid. When the dicarboxylic acid powder consists of two or more dicarboxylic acids, with the dicarboxylic acid powder consisting of a physical mixture of two or more dicarboxylic acid powders, the salt-preparation step (i) may likely result in a physical mixture of two or more DD-salts. In that case the powder temperature shall be below the lowest of the melting temperature of the DD-salt with the lowest melting temperature and the melting temperature of the dicarboxylic acid with the lowest melting temperature.

In step (i) the diamine is dosed as a liquid to the agitated powder. In cases, wherein the diamine is solid at room temperature, it may be necessary to first melt the diamine for the preparation of the liquid diamine.

Upon dosing of the diamine, the diamine and the dicarboxylic acid in the agitated powder form a reaction mixture, which gradually changes in composition, initially comprising the dicarboxylic acid, over time changing from mixed dicarboxylic acid and diamine/dicarboxylic acid salt, and finally resulting in a diamine/dicarboxylic acid salt powder.

In step (ii) of the process according to the invention the diamine/dicarboxylic acid salt is polymerized in the solid-state to produce the polyamide. Preferably the DD-salt is polymerized in the form of the powder obtained from step (i).

With the term solid-state polymerization is herein understood that the polymerization is carried out under conditions such that the DD-salt, the polyamide and any intermediate condensation product thereof remain in the solid state. This is accomplished by using reaction temperatures for the condensation step(s) below the melting temperature of the DD-salt, respectively below the melting temperature of the polyamide, and any intermediate product thereof.

When the process is not carried out in the solid state, this can lead to fusion of particles, resulting in lump formation and cohesive powder flow. The temperature, at which the reactants start to become mechanically deformable, upon which these phenomena occur, referred to as softening temperature, is dependent on process and process conditions, and is therefore best determined under real life process conditions, e.g. either on lab scale, pilot scale or plant scale. This can be done by experiments, at different temperatures, approaching the softening temperature from below. In stirred process equipment, the softening temperature is reflected, for example, in a steep increase in measured torque during heating when reaching the softening temperature from below. In static polymerization experiments, reaching the softening temperature can be observed, for example, from samples showing lumps of molten and fused particles. For the solid-state polymerisation in the process according to the invention softening is avoided by applying condensation conditions well below the melting temperature of the DD-salt, polyamide and intermediate products thereof.

With the term melting temperature (Tm), as used herein, unless expressed otherwise, is herein understood the peak temperature of the endothermic melting peak measured by DSC by the method according to ISO 11357-1/3 (2009) with a scan rate of 20° C./min in the first heating cycle.

The salt-preparation in an agitated powder, as well as the solid-state polymerization thereof, is carried out in the solid state. This does not exclude that during the process liquid components may be added or formed. First of all diamine can be added as a liquid for the salt preparation. Liquid diamine may also be added, for example during the solid-sate polymerization step (ii). The diamine used in step (i) may contain some water. Also water may be formed upon reaction of amines and carboxylic acid groups during the polymerization, which water can evaporate and condense. During the salt-preparation, also some water may be present in the starting materials or being formed during the dosing step. Small amounts of water are not a problem as long as it is possible to maintain an agitated powder. The water may be removed by evaporation during the salt preparation or later on during the heating in the solid-state polymerization.

The powder comprising the DD-salt as prepared in step (i) may comprise water, for example about 7.5 wt. %, or even higher, such as water of crystallisation, while still retaining an agitated powder. Preferably, the powder comprises at most 5 wt. % of water, more preferably at most 2.5 wt. % or even better at most 1.0 wt. % or 0.5 wt. % water, wherein the wt. % (weight percentage) is relative to the total weight of diamine and dicarboxylic acid in the DD-salt.

In the salt-preparation step (i), the diamine is dosed as a liquid. The dosing of the diamine in liquid form in the salt-preparation step automatically implies that the diamine is dosed at a dosing temperature, i.e. the temperature of the diamine at the moment of dosing, above the melting temperature of the diamine and below the boiling temperature of the diamine. The boiling temperature is measured at the pressure conditions applied at the moment of dosing.

The diamine may consist of a mixture of two or more diamines. In case that a diamine mixture is used, the melting temperature, boiling temperature and dosing temperature of the diamine are based on the diamine mixture.

For the DD-salt preparation, the powder temperature during dosing is preferably at least 40° C. below the melting temperature of the DD-salt (Tm-salt), more preferably at least 60° C. below Tm-salt. Using a powder temperature further below Tm-salt reduces the potential occurrence of premature reaction of the diamine and dicarboxylic acid. The powder temperature is also preferably kept below 220° C.; more preferably below 180° C. With an aliphatic dicarboxylic acid being present in the agitated powder, the powder temperature is preferably below 150° C., and more preferably below 130° C. The powder temperature is also suitably below the boiling temperature of water. Herein the boiling temperature is measured at the pressure conditions applied at the moment of reaction. Using a lower powder temperature reduces the problem of freed gaseous water being condensed in cold spots and scaling of powder on such spots. Such a lower powder temperature is also favourably applied for DD-salts that are more prone to low temperature reaction and to sticking of particles due to softening by the water, as can be the case in particular for salts of aliphatic dicarboxylic acids.

The powder temperature is also preferably kept above 0° C. This reduces the risk of freezing of water, in case of water being present in the reaction mixture for the salt preparation. The powder temperature is more preferably at least 20° C., to allow heat removal through a cooled wall without freezing components to that wall.

The diamine is dosed to the agitated powder to form a powder reaction mixture meanwhile retaining an agitated powder. Thus, the diamine is preferably not added and mixed at once with the dicarboxylic acid in the agitated powder, as this could be incompatible with retaining an agitated powder, and could also lead to lumping of wetted parts and incomplete neutralization of non-wetted parts. This would severely complicate and even inhibit the proper mixing and homogenization of the reacting components. The dosing rate is suitably limited to prevent local accumulation of liquid diamine, thereby preventing excessive wetting, local overheating and premature reaction with release of water resulting in excessive sticking and complicating moving of the bed. This way of dosing is preferred and expressed with the term "gradually dosing".

As an indication, the diamine liquid is suitably gradually dosed in a time period in the range of about 25 minutes to about 36 hours, for example in the range of in the range of about 1 to 20 hours, suitably 2 to 10 hours. A shorter dosing time than 25 minutes may be applied, for example 20 minutes, as long as the agitated powder is retained. However, in particular when carried out on larger scale, this may be more difficult. A longer dosing time than 36 hours may be applied, for example 48 hours, or longer. However, such a long dosing time is less preferred for economic reasons.

The diamine is also suitably dosed with an average dosing rate between 0.05 mole % of diamine per minute (mppm) (corresponding with an overall dosing time of 33.3 hours) and 5 mole % (20 minutes) of diamine per minute (mppm), preferably between 0.1 mppm (16.7 hours) and 4 mppm (25 min), for example between 0.2 mppm (8.35 hours) and 2 mppm (50 min), or between 0.25 mppm (6.7 hours) and 1 mppm (100 minutes), wherein the mole % of diamine is relative to the molar amount of dicarboxylic acid. The times between brackets indicate the corresponding dosing time.

Long dosing times, respectively low dosing rates, may be used, and will allow more time for the diamine to react with the dicarboxylic acid, and is favourably used to prevent creating softening or sticking of the acid or solid DD-salt, but might make the process less economical. Short dosing times, respectively higher dosing rates may be used, where applicable, however, more power or special mixer designs may be needed for good mechanical agitation of the dicarboxylic acid and the reaction mixture to achieving effective dispersion of the diamine in the reaction mixture and for removal of heat from the mixing and heat resulting from the salt formation reaction between diamine and dicarboxylic acid, in order to prevent sticking and caking of the reaction mixture. Suitable dosing rates for individual case can be determined by routine experiments with, for example, variation in the dosing rate.

In another embodiment of the invention, the salt-preparation step (i) comprises contacting a diamine with a dicarboxylic acid to provide a reaction mixture in which said diamine and said dicarboxylic acid react to form a diamine/dicarboxylic acid salt, wherein:
  (a) the dicarboxylic acid comprises an aromatic dicarboxylic acid;
  (b) the dicarboxylic acid is provided in a powder form;
  (c) the diamine is provided in a liquid form;
  (d) the contacting is performed by gradually dosing diamine liquid to dicarboxylic acid powder, while keeping the dicarboxylic acid powder in constant movement;
  (e) the reaction mixture is kept in constant movement for a time period directly following completion of the dosing,
  (f) (d) and (e) are carried out at a temperature above 0° C. and below all of the following: the boiling temperature of the diamine and the melting temperatures of the dicarboxylic acid, the diamine/dicarboxylic acid salt and any intermediate reaction product, and
  (g) in (d) and (e) the reaction mixture comprises at most 5 wt. % of water, relative to the total weight of the diamine and dicarboxylic acid.

The effect of this embodiment of the process according to the invention is that the DD-salt is obtained in solid particulate form being substantially anhydrous. By "substantially anhydrous" is meant herein that the DD-salt generally contains no more than 5 wt. % of water, relative to the total weight. The DD-salt is recovered from the process is a stable, substantially free flowing powder. The DD-salt is obtained as a generally homogenous product, suitable for use in common commercial processes for the manufacture of polyamide polymers. This result can be achieved without a precipitation step involving using an organic solvent and without the use of a cryogenic medium in the reaction mixture. The process does not require high shear mixing, and the process can easily be scaled up to industrial scale.

The DD-salt may still contain some unreacted dicarboxylic acid, for example, if less than an equivalent amount of diamine was used. The DD-salt may also contain some unreacted diamine, for example, if more than an equivalent amount of diamine was used. It has been observed that the DD-salt may contain some excess diamine and still show the characteristics of a dry solid powder.

The DD-salt formed in step (i) can be an equimolar salt, but does not necessarily have to be an equimolar salt. Even when (near) stoichiometric amounts of diamine and dicarboxylic acid are used, unreacted dicarboxylic acid and unreacted diamine may co-exist in the DD-salt, as might be witnessed by X-ray diffraction (XRD) measurements for the aromatic dicarboxylic acid, and analysis by gas chromatography with a head-space sampler for the diamine in the DD-salt. Surprisingly, this does not appear to have a significant effect on the solid-state polymerization, as these reactants largely find each other in the remainder of the process, and result in products with hardly any residual dicarboxylic acid as witnessed by XRD, in combination with a relatively high molecular weight or viscosity.

It has further been observed that in case of excess of diamine the molar balance is at least in part corrected during the first part of condensation, or step (ii-a), by evaporation of diamine, whereas in case of excess of dicarboxylic acid it is possible to correct the molar balance during the second part of the condensation, or step (ii-a) of the process, by addition of diamine during that step.

It has been observed that for salt preparation with a large deficiency in diamine, for example with a diamine/dicarboxylic acid molar ratio around 0.75-0.85, it is still possible to correct the diamine deficiency by adding excess diamine during the solid-state polymerisation, and obtain a polyamide with sufficiently high molecular weight. Therefore, the solid DD-salt used in the processes according to the invention suitably has a diamine/dicarboxylic acid molar ratio of at least 0.75. Preferably the diamine/dicarboxylic acid molar ratio is in the range of 0.75-1.10, more preferably 0.90-1.10, even more preferred 0.95-1.05, and most preferably 0.98-1.02. With a diamine/dicarboxylic acid molar ratio closer to 1 has the advantage that the diamine is used in a more efficient manner.

The salt-preparation step (i) can be carried out in different ways and different types of reactors. Suitably, the diamine and the dicarboxylic acid are contacted by spraying or dripping the diamine onto the moving dicarboxylic acid powder. In a batch wise operation, suitably, the diamine and the dicarboxylic acid are contacted by spraying or dripping the diamine onto the moving dicarboxylic acid powder, subsequently spraying or dripping the diamine onto the moving mixture of formed DD-salt and dicarboxylic acid powder after addition of the diamine has started. Suitable reactors, in which the diamine and the dicarboxylic acid can be contacted and mixed, are, for example, tumble mixers, ploughshare mixers, conical mixers, planetary screw mixers and fluidized bed reactors. These mixers are examples of low shear mixers. Although high-shear mixers in principle could also be used, they are not preferred for reasons of higher energy consumption, additional cooling requirements of the reacting mixture, attrition and possibly increased agglomeration of overwetted parts. Further information on these and other low shear mixer apparatus can be found in the book "Handbook of Industrial Mixing—Science and Practice" edited by: Paul, Edward L.; Atiemo-Obeng, Victor A.; Kresta, Suzanne M. (Publisher: John Wiley & Sons; 2004; ISBN: 978-0-471-26919-9; Electronic ISBN: 978-1-60119-414-5), more particularly in Chapter 15, Part 15.4 and 15.11.

The temperature in the reactor may be controlled by conventional measures. Heat produced upon neutralisation reaction of the diamine and the dicarboxylic acid to form the diamine/dicarboxylic acid salt may be removed. For the removal conventional measures may be applied, for example, a heat exchanger, a cooled wall, a cooled agitator, or a gas flow or a combination thereof.

The salt-formation reaction itself appears to be sufficiently fast to also allow continuous salt production in suitable equipment in an economical way. For instance, such a process could be built around a continuously fed mixing-screw in a pipe or trough, with auxiliary dosing equipment. In a continuous operation for the salt preparation, suitably, the diamine and the dicarboxylic acid are contacted by spraying or dripping the diamine onto the agitated dicarboxylic acid powder in a mixing zone.

The fact that the salt-preparation step in the process according to the invention can be carried out without applying a high shear and still provide a high degree of conversion is highly surprising. In fact, the creation of an agitated powder can be accomplished with low shear agitation avoiding attrition of the dicarboxylic acid powder. In fact the attrition can be so low, or even absent at all, that the particle size distribution is hardly affected, apart from the fact that the size of the dicarboxylic acid powder particles generally increases during the reaction with the diamine. The advantage of such low shear agitation without attrition of the dicarboxylic acid powder, is that the amount of fines produced during the process is low, and that problems of fouling, dusting, sagging upon storage, and reduced flowability due to clogging by fines is reduced.

Favourably, the dicarboxylic acid powder used in the process according to invention comprises a small fraction of particles with small particle size. Also favourably, the dicarboxylic acid powder has a narrow particle size distribution. For example, the dicarboxylic acid powder has a particle size distribution with a d10 of at least 15 μm and a d90 of at most 1000 μm. Herein the particle size distribution is measured with laser granulometry by the method according to ISO 13320 at 20° C. The use of dicarboxylic acid powder with a small fraction of small particles and/or narrow particle size distribution, is favourably combined with low shear agitation. The advantage thereof is that the resulting DD-salt so produced also has fewer small particles, respectively a relatively narrow particle size distribution, and optionally even better flow properties.

Preferably the d10 for the particle size distribution of the dicarboxylic acid powder is in the range of 15-200 μm, more preferably in the range of 16-160 μm. Preferably, the d90 is in the range of 100-1000 μm, more preferably in the range of 150-800 μm. Suitably, the dicarboxylic acid powder also has a median particle size (d50) in the range of 40-500 μm. Preferably, the d50 is in the range of 40-400 μm. Also preferably the dicarboxylic acid powder has a particle size distribution with a Span, defined by the ratio of (d84-d16)/d50, of at most 5. The advantage is that also the resulting DD-salt has a narrower particle size distribution and the flow is further improved.

Starting with a dicarboxylic acid powder with a narrow particle size distribution and applying a low shear mixing it is possible to obtain a salt powder with a good flowability.

Favourably, the solid DD-salt has a flowability (ffc) of at least 4, more preferably at least 7. The flowability is herein defined by the ratio σ1/σc, of consolidation stress, σ1, to unconfined yield strength, σc, measured by the shear test method according to ASTM D6773. In a particular embodiment of the invention the solid DD powder is a free flowing powder, i.e. having a flowability (ffc) of at least 10. Salt powders with such good flowability are more easily obtained starting with at least 50 mole % of aromatic dicarboxylic acid, wherein the mole % is relative to the total molar amount of dicarboxylic acid in the powder bed. The remaining fraction of the dicarboxylic acid can be an aliphatic dicarboxylic acid. If combined with an aliphatic diamine, the resulting salt powder comprises a mixture of an aromatic DD-salt and an aliphatic DD-salt. Preferably, the DD-salt is purely based on an aromatic dicarboxylic acid. I.e. the DD-salt in the powder resulting from step (i) consisting of aromatic DD-salts.

In another particular embodiment the solid DD-salt powder has a particle size distribution, measured by the method according to ISO 13320, with a d10 of at least 20 μm (micro-meters), and a d90 of at most 1000 μm. Suitably, said granules have a median particle size (d50) in the range of 50-600 μm. Preferably, the solid DD-salt has a particle size distribution, wherein the d10 is in the range of 20-200 μm, the d50 is in the range of 50-500 μm, and the d90 is in the range of 200-1000 μm. Also preferably, the DD-salt has a particle size distribution with a Span, defined by the ratio of (d84-d16)/d50, of at most 5, preferably at most 2.5. Salts with such particle size distribution can be obtained from dicarboxylic acid with a relative narrow particle size distribution and a small amount of fines in combination with the low shear mixers mentioned above.

Also favourably, the solid DD-salt powder has a compressibility, expressed by the ratio of (TBD−ABD)/TBD*100%, of at most 35%, wherein ABD is the aerated bulk density and TBD is the tapped bulk density both measured by the method according to ASTM D6393.

Each of the properties of low content of fines, narrow particle size distribution, high flowability and low compressibility are favourable for the process as described in claim 1 without further shaping of the solid DD-salt in between step (i) and step (ii) as described below.

The solid DD-salt obtained by step (i) is a polycrystalline salt powder consisting of powder particles comprising multiple micro-crystallites. The salt generally has a relative large surface area, in relation to the size of the powder particles. The DD-salt powder may well have a high BET value of at least 0.5 $m^2$/g, or more particular at least 0.8 $m^2$/g. Herein the BET value is measured by the method according to ISO 9277:2010.

The salt preparation step (i) and the polymerization step (ii) in the process according to the invention may be carried out in a single reactor or in different reactors.

In a preferred embodiment the preparation of the solid DD-salt in step (i) and the polymerization step (ii) are carried out as an integral process carried out in a single reactor. This has the advantage that the number of handling steps is reduced. A further advantage is that in case the salt is prepared at elevated temperature, energy can be saved by omitting cooling of the salt after step (i) and reheating for step (ii).

Alternatively, after the salt preparation, the salt may be transferred from a first reactor, referred to as dosing/mixing reactor, to another reactor, the polymerization reactor.

In a special embodiment, the DD-salt is subjected to a solid-state shaping step before the salt is subjected to polymerization step (ii). By applying a solid-state shaping step, the salt retains its polycrystalline structure comprising multiple micro-crystallites, or substantially so. In the solid-state shaping step, the salt powder may, for example, be granulated to form granules, or be compacted into pellets. Likewise, the polyamide resulting from the condensation step is obtained, respectively, as granules or as pellets.

Such solid-state shaping step can be advantageous for further processing of the solid-state polymerization in a batch process in a static bed reactor, such as a static column filling; or in a continuous process with a moving column filling, as well as for further downstream applications of the polymer so obtained in melt processes. Advantages of larger particles in the process are reduced entrainment of powder by any gases in the process, albeit reaction water, sweep gases or gases used for heating the reactants. Advantages after reaction are in improved flow properties for handling in silo's and big-bags, and easier and high capacity feeding of melt extruders that are used for subsequent processing of thermoplastic polymers.

Granulation can be done by spraying a binder onto the powder while keeping the powder in motion, applying e.g. fluid-bed granulation, high-shear granulation or drum granulation. Pelletization can be done by e.g. gear pelletizing, roller compaction, tableting, or solid-phase extrusion. Examples of these processes can be found in the Handbook of Powder Technology, vol. 11 Granulation, Edited by A. D. Salman, M. J. Hounslow, J. P. K. Seville, Elsevier © 2007, ISBN 978-0-444-51871-2. In each of these processes water, amines or salt solution or a mixture of these can suitably be used as a binder, since these substances do not introduce foreign chemicals into the polymerization mixture. Other suitable binders, such as solutions of polyvinylpyrrolidone (PVP), polyethylene glycol (PEG) and polyvinyl alcohol (PVA), are not excluded. Typically a few weight percentage of binder, e.g. 1-5 wt. %, is used, relative to the weight of the powder.

Granules and pellets will typically be of larger size than the powder particles, as each of these granules and pellets will comprise multiple powder particles. Suitably, the granules will have a particle size of from sub-millimeter to centimeter scale, generally from about 0.5 mm to 4 cm, for example from about 2 mm to about 2 cm. Suitably, the pellets will have a main diameter of a few millimeters, for example from about 1 to 8 mm, such about 2-5 mm. Suitably, the pellets will have a particle size of from millimeter to centimeter scale, generally from about 1 mm to 1 cm, for example from about 2 mm to about 5 mm.

In the process of the present invention the solid DD-salt is subjected to solid-state polymerization to obtain the polyamide. This solid-state polymerization can be carried out using conditions known to be suitable for direct solid-state polymerization for preparing polyamides.

The condensation temperature in step (ii) is at least initially, and eventually throughout this condensation step, is kept below the melting temperature of the DD-salt (Tm-salt). Suitably, the condensation temperature herein is at least 10° C., preferably at least 15° C. below Tm-salt, more preferred at least 20° C. below Tm-salt.

According to a first preferred aspect of the invention, step (ii) comprises two sub-steps:
 (ii-a) condensing the DD-salt obtained in step (i) at a first condensation temperature (Tc1) at least 10° C. below the melting point of the DD salt salt to produce a solid prepolymer; and
 (ii-b) condensing the solid prepolymer resulting from step (ii-a) further at a second condensation temperature (Tc2) at least 15° C. below the melting temperature of the prepolymer and the melting temperature of the polyamide to be obtained,
thereby obtaining the polyamide in a solid state.

The advantage of this first preferred aspect of the invention is that the process can be carried out at high reaction temperatures, meanwhile achieving high reaction rates, surprisingly resulting in the preparation of semi-aromatic polyamides in a high yield, with a high degree of polymerization in relative short reaction time, without occurrence of gelation. The effect of this aspect of the invention is an overall very efficient production process, allowing for high utilization of production capacity. This result can be achieved even without the need to add a catalyst, and despite the fact that the carboxylic acids comprise primarily aromatic dicarboxylic acid.

Thus, in the first sub-step the condensation temperature is kept at least 10° C. below the melting temperature of the DD-salt (Tm-salt), and in a second or further sub-step the condensation temperature may be raised, eventually even above the melting temperature of the DD-salt, while being kept below the melting temperature of the prepolymer, the melting temperature of the polyamide to be obtained and the melting temperature of any intermediate condensation product thereof. Suitably, the condensation temperature in such second or further sub-step is at least 15° C., preferably at least 20° C., more preferred at least 25° C. below the melting temperature of the polyamide and any intermediate condensation product thereof.

Rather than applying discrete sub-steps, the process may also be carried out by applying a temperature gradient going gradually from a condensation temperature at least 10° C. below Tm-salt to a higher temperature while remaining at least 15° C. below the melting temperature of the polyamide and any intermediate condensation product thereof.

In case of a salt powder obtained from step (i) comprising a mixture of different DD-salts, these salts might possibly have different melting temperatures and different condensation rates at a given temperature. This may be the case, for example, if the salt powder comprises a mixture of an aliphatic DD-salt and an aromatic DD-salt. In the case that the DD-salt with the lowest melting temperature would have the highest condensation rate, step (ii) may be carried out in two sub-steps, wherein in a first sub-step the salt with the lowest melting temperature is condensed to a polyamide prepolymer at a temperature at least 10° C. below the lowest of the said salt melting temperatures, and then the temperature may be raised while remaining at least 15° C. below the melting temperature of said prepolymer and at least 10° C. below the melting temperature of other salt and at least 15° C. below the melting temperatures of any further polyamide prepolymers and any intermediate products thereof. In the case that the DD-salt with the lowest melting temperature would have the same or a lower condensation rate, Tc1 in step (ii-a) will remain below the lowest of the salt melting temperatures.

It is noted that Tc1 and Tc2 are not necessarily different, these may be the same. If different, Tc2 is preferably higher than Tc1, and more preferably also higher than Tm-salt, as this will result in a higher condensation rate.

With a prepolymer is herein understood a polyamide condensation product having a viscosity number of at least 8 ml/g. Prior to raising Tc2 above Tm-salt, the prepolymer preferably has a viscosity number of at least 10 ml/g, more preferably at least 15 ml/g, and even better at least 20 ml/g.

Preferably Tc1 is at least 210° C., more preferably, Tc1 is above 220° C., more preferably at least 230° C., even more preferably at least 240° C. A higher reaction temperature for Tc1 results in faster reaction and shorter reaction times.

Preferably Tc2 is at least 240° C. Also in a preferred embodiment, Tc2 is at least 25° C. below the melting temperature of the prepolymer, polyamide and any intermediate condensation product thereof.

Herein the viscosity number is measured in 96% sulphuric acid (0.005 g/ml) at 25° C. by the method according to ISO 307, fourth edition.

In step (ii-b) the polyamide prepolymer is further condensed to obtain the polyamide of desired molecular weight.

The duration of the step (ii-b) will depend on the processing conditions and desired degree of polymerization. The expression "desired degree of polymerization" is not bound to a method or number. The desired degree of polymerization will usually depend on the intended use of the polyamide. It may be determined by any suitable method. For example, the degree of polymerization may be determined as a polymer property such as viscosity, mechanical properties, or molecular weight. The degree of polymerization may also be derived from the conversion of the carboxylic acid groups and amine groups and expressed, for example, by the ratio $1/(1-p)$. Herein the conversion p is the molar fraction of the carboxylic acid groups and amine groups reacted, relative to the initial total molar amount of these functional groups initially present in the DD-salt.

The condensation step (ii), as well as each of the sub-steps (ii-a) and (ii-b) may be carried out in any manner suitable for conventional SSP processes, for example, in a static bed reactor, in a moving bed reactor, or in an agitated reactor. An agitated bed reactor, such as a rotating vessel or a mechanically stirred reactor, wherein the solid DD salt and solid prepolymer are agitated, and thereby kept in motion and circulated, is preferred for step (ii-a) in case of lower melting DD-salts, and for DD-salts that are more prone to sticking upon release of water, such as is the case for aliphatic DD-salts. Use of an agitated bed reactor, contributes to the result that the polymer obtained by the process is a non-sticky powder or granulate material. The polyamide powder is eventually even free flowing. For the second condensation step (ii-b) a static bed reactor, such as a batch wise operated vertical column reactor, or a moving bed reactor, such as a continuously operated vertical column reactor, might be an economically better alternative.

The salt-preparation step (i), as well as solid-state polymerization (ii) in the process according to the invention are suitably carried out in an inert gas atmosphere. For the inert gas atmosphere, suitable gases as generally known in the art for the polymerization of polyamides can be used. Such inert gas is typically oxygen-free or essentially so, and free of other oxidative reactive gasses such as O3, HNO3, HClO4, etc. Suitably, nitrogen gas is used as the inert gas. The salt-preparation as well as the polymerization steps are suitably carried out at atmospheric pressure, or at a slight overpressure, for example in the range between 1 and 5 bar, for example at about 1.5 bar, or 2 or 3 bar. Using an overpressure has the advantage that diamine losses during salt preparation are reduced, if occurring at all.

The process can be performed with an inert gas purge, suitably nitrogen gas, during salt-preparation step (i) and more advantageously during the solid-state polymerization, step (ii). An inert gas purge can be applied to remove any water initially present in the DD-salt during heating prior to the solid-state polymerization. An inert gas purge is also contributing to effective removal of water resulting from the condensation reaction, thereby reducing the risk of sticking (caking) of the reaction mixture and help, for example, to prevent blocking of pressure release valves, measuring lines and other (purge) lines into the process and to protecting mechanical seals. The appropriate level of the gas purge is suitably chosen on the basis of economics and efficiency, and can be determined by routine experiments.

The heating and cooling may be accomplished by heating the inert gas used for the purge, or by heating the reactor walls or internals therein, or any combination thereof. The heating is preferably done using temperature ramps for the heating. This results in a gradually increase in temperature of the reactor content, and a gradient for the condensation reaction temperatures. The advantage thereof is that water produced from the condensation reaction is released over a longer time, and more easily removed thereby minimizing the chances of scaling.

The solid-state polymerization step (ii) can be carried out, for example, as follows. The DD-salt is prepared in, or alternatively charged to a polymerization reactor. The DD-salt is suitably first heated with a first temperature ramp to a set temperature in the range of 100-160° C., suitably around 130° C., to allow any water in the DD-salt being released by evaporation and being carried away via the purge gas, meanwhile keeping the temperature of the reactor wall and internals therein at the same temperature or above to avoid condensation on the surfaces. The solid DD-salt is suitably staged at that set-temperature for as long as is necessary to remove the water in the DD-salt. This may be checked, for example by means of a water trap. Once the water removal is complete, or nearly so, the solid DD-salt is heated with a second temperature ramp to a set point equal to Tc1. The first condensation step may be tracked by the water condensate formation rate which starts slowly and then increases. The prepolymerization typically runs until the condensate collection rate drops significantly. The completeness of the conversion of the DD-salt can also be checked with DSC by absence of residual melting enthalpy for the melt peak of the DD-salt. For the second condensation step the solid prepolymer formed may either be kept at the same temperature, i.e. Tc2 being equal to Tc1, or be further condensed at a lower temperature, or may be heated by a third temperature ramp to a set point equal to Tc2 and being higher than Tc1. The polyamide is kept at that temperature until the desired degree of polymerization is obtained. Once the polymerization is complete, the polymer is cooled and discharged from the reactor.

It has been observed that the loss of diamine during the first condensation step (ii-a) is rather limited. In case of a DD-salt with a diamine/dicarboxylic acid molar ratio above one, the loss is generally not much more than the amount corresponding with the excess of diamine. In case of a DD-salt with a diamine/dicarboxylic acid molar ratio around or below one, the loss is generally in the order of only a few percentages, if not less. The deficiency in diamine that might result has not been observed to reduce the reaction rate. An advantage of the process according to the invention is that the process is not so critical for loss of a small amount of diamine with respect to polymerization rate. Attainment of a medium-to-high molecular weight polymer is easily achieved. Suitably, the polyamide so obtained has a viscosity number of at least 20 ml/g, preferably at least 35 ml/g, more preferred at least 50 ml/g, or even at least 65 ml/g.

The degree of polymerization can be increased by limiting the gas stream in the first condensation step. For obtaining a higher degree of polymerization it might be advantageous to add diamine during the solid-state polymerization. Suitably, supplemental diamine is added by spraying liquid diamine onto the reacting components or by introducing diamine as a gas via the inert gas purge. This may done be, for example, during step (ii-a), or during step (ii-b), or any combination thereof.

Adding diamine during step (ii-b) is favourably applied for branched diamines that typically would form lower melting salts, even with aromatic dicarboxylic acids like terephthalic acid. Branched diamines are diamines that comprise one or more alkyl groups along the alkylene diamine monomer back bone. Examples of branched aliphatic diamines are 2,2-dimethyl-1,3-propanediamine, 2-methyl-1, 5-pentamethylenediamine, 2-methyl-1,9-nonane diamine, trimethyl-1,6-hexamethylenediamine and isophoronediamine.

In a preferred embodiment of the process according to the invention, supplemental diamine is added during the second condensation step (ii-b).

In another preferred embodiment of the process, during the second condensation step, a mono-functional monomer is added. Suitably, the monofunctional monomer is a mono-functional amine, for example dodecylamine, or a mono-functional carboxylic acid, for example benzoic acid. The advantage of the adding the chain stopper is that the process allows obtaining a high molecular weight polyamide in reasonable short time, while at the same time the polyamide has very good melt stability in terms of viscosity retention during melt processing. The amount of monofunctional monomer is suitably at most 2.0 mole %, preferably at most 1.0 mole %, relative to the total molar of dicarboxylic acid.

It is also possible to add trifunctional or higher functional monomers, which are preferably added during the second condensation step. Such monomers can act as branching agent. In order to prevent excessive branching and gelation, the amount of such monomers is suitably at most 1.0 mole %, preferably at most 0.5 mole %, relative to the total molar amount of dicarboxylic acid.

Where appropriate, a combination of supplemental diamine and/or a chain stopper and/or a tri/higher functional monomer is added.

In the process according to the invention the solid DD-salt may comprise small amounts of catalyst without lowering the melting point of the salt too much, and still achieving the effects of the invention. However, the amount should be limited such that Tm-salt is not below 265° C. Preferably the solid DD-salt is prepared without a phosphorous containing polycondensation salt.

In the process of the invention an AA-BB polyamide is made by solid-state polymerization of a diamine/dicarboxylic acid salt (DD-salt) prepared from diamine and dicarboxylic acid comprising an aromatic dicarboxylic acid.

The DD-salt provided in step (ii) of the process according to the invention is obtained by dosing a diamine to an agitated powder comprising an aromatic dicarboxylic acid. The diamine suitably consists of one diamine, or a mixture of at least two diamines. The dicarboxylic acid may also consist of one dicarboxylic acid, or comprise a mixture of at least two dicarboxylic acids. Suitably, the DD-salt is a salt of at least one aromatic dicarboxylic acid and a mixture of at least two diamines.

The DD-salt may also be a physical mixture of two different salts. Such a physical mixture may be prepared by using an agitated powder comprising a physical mixture of at least two dicarboxylic acids. Alternatively, the physical mixture may be prepared by first separately preparing the salts according to step (i), thus each comprising dosing a diamine to an agitated powder comprising an aromatic dicarboxylic acid as in step (i), and mixing the salts prior to step (ii).

Suitably, the aromatic dicarboxylic acid comprises terephthalic acid, 2,6-naphthalene dicarboxylic acid and biphenyl-4,4'-dicarboxylic acid, or a combination thereof. Preferably, the aromatic dicarboxylic acid is selected from terephthalic acid, 2,6-naphthalene dicarboxylic acid and biphenyl-4,4'-dicarboxylic acid. These preferred aromatic dicarboxylic acids favour the formation of the DD-salt as a solid powder and result in DD-salts with higher melting temperatures allowing higher processing temperatures. Even more preferably the dicarboxylic acid comprises or even consists of terephthalic acid.

The dicarboxylic acid from which the DD-salt is prepared may also further comprise an aliphatic dicarboxylic acid. The aliphatic dicarboxylic acid suitably is a non-cyclic dicarboxylic acid, either linear or branched, or a cyclic dicarboxylic acid, or a combination thereof. Suitably the aliphatic dicarboxylic acid is an aliphatic dicarboxylic acid having 4-8 carbon atoms. Also suitably the aliphatic dicarboxylic acid is chosen from the group of 1,4-butanedioic acid (also known as succinic acid), 1,6-hexanedioic acid (also known as adipic acid), 1,8-octanedioic acid (also known as suberic acid) and 1,4-cyclohexanedicarboxylic acid.

Preferably, the aliphatic dicarboxylic acid comprises, or more preferred consists of adipic acid, or trans-1,4-cyclohexanedicarboxylic acid, or a combination thereof. Adipic acid is the most widely used aliphatic dicarboxylic acid in semi-crystalline polyamides and trans-1,4-cyclohexanedicarboxylic acid can be used for preparing semi-crystalline polyamides with higher melting points.

The aliphatic dicarboxylic acid and aromatic dicarboxylic acid are suitably present as a physical mixture of powders of each of the dicarboxylic acids. In that case the salt-preparation step will result in a physical mixture of salts, as can generally be confirmed by observation of different melting temperatures of the salts in DSC measurements.

In a preferred embodiment of the invention, the dicarboxylic acid consists of (a) an aromatic dicarboxylic acid selected from terephthalic acid, 2,6-naphthalene dicarboxylic acid and biphenyl-4,4'-dicarboxylic acid, or a combination thereof; (b) optionally an aliphatic dicarboxylic acid, selected from adipic acid and cyclohexane dicarboxylic acid, or a combination thereof; and (c) at most 10 mole % of another dicarboxylic acid, relative to the total molar amount of dicarboxylic acid.

Preferably, the aromatic dicarboxylic acid constitutes an amount of at least 50 mole %, relative to the total molar amount of dicarboxylic acid in the agitated powder in step (i) according to the invention. Consequently in the DD-salt resulting therefrom the dicarboxylic acid in the DD-salt will comprise at least 50 mole % of an aromatic dicarboxylic acid, relative to the total molar amount of dicarboxylic acid in the DD-salt. The advantage is that salt-preparation step (i) allows for much easier preparation of an easy flowing powder. A further advantage is that the time needed in the first condensation step (i) before the temperature can be raised without sticking problems, can be further decreased, thus allowing faster polycondensation of aromatic DD-salt and shortening the overall polymerization time with respect to a mixture wherein the amount of the aromatic dicarboxylic acid is less than 50 mole %.

More preferably, the dicarboxylic acid in the agitated powder in step (i), respectively in the DD-salt in step (ii) comprises at least 75 mole % of aromatic dicarboxylic acid, relative to the total molar amount of dicarboxylic acid. Having higher contents of aromatic dicarboxylic acid allows higher condensation reaction temperatures and a faster conversion to polyamide without fouling the reactor and/or forming lumps.

Most preferred, the dicarboxylic acid consists essentially of aromatic dicarboxylic acid i.e. for at least 99 mole %, or consists of aromatic dicarboxylic acid, wherein the aromatic dicarboxylic acid is selected from terephthalic acid, 2,6-naphthalene dicarboxylic acid and biphenyl-4,4'-dicarboxylic acid; or a combination thereof. This allows even higher heating rates and condensation reaction temperatures and even shorter reaction times.

The diamine used in the process according to the invention is suitably selected from aliphatic diamines and aliphatic-aromatic diamines or a combination thereof. Aliphatic-aromatic diamines are diamines wherein each of the amine groups are directly connected to an aliphatic moiety, and which aliphatic moieties in turn are connected to an aromatic moiety.

The aliphatic diamine may comprise a linear aliphatic diamine, a branched aliphatic diamine or a cyclo-aliphatic diamine, or a combination thereof.

The aliphatic diamine suitably comprises a C2-C10 diamine, i.e. a diamine having from 2 to 10 carbon atoms. The C2-C10 aliphatic diamine is suitably selected from 1,2-ethylenediamine, 1,3-propanediamine, 1,4-butanediamine, 1,5-pentanediamine, 1,6-hexanediamine, and 1,4-cyclohexanediamine, which are examples of C2-C6 diamines; and 1,7-heptane diamine, 1,8-octanediamine, 1,9-nonane diamine, and 1,10-decane diamine, which are examples of C7-C10 diamines.

Preferably, the aliphatic diamine comprises a C4-C6 diamine, such as 1,4-butanediamine, 1,5-pentanediamine, 1,6-hexanediamine, trans-1,4-cyclohexanediamine.

More preferably the diamine comprises a linear C4-C10 diamine, more particular, 1,4-butanediamine, 1,5-pentanediamine, and 1,6-hexanediamine, or trans-1,4-cyclohexanediamine or a combination thereof. This will lead to a DD-salt with a higher melting point, allowing higher condensation reaction temperatures while limiting the risk of sticking of particles.

Also more preferably, the diamine comprises at least 50 mole % of the C2-C6 diamine, and even more preferred at least 75 mole %, relative to the total molar amount of diamine in the DD-salt. This also leads to salts and copolyamides with higher melting temperatures thereby allowing higher processing temperatures without increasing the risk of sticking during condensation steps (ii-a) and (ii-b).

The DD-salt prepared from the aromatic dicarboxylic acid suitably has a melting temperature of at least 240° C. (wherein ° C. is degrees Celsius), more preferably of at least 250° C., for example in the range of 260-330° C.

Examples of such salts include XY salts wherein X is a C2-C10 diamine, or a combination thereof, and Y is selected from terephthalic acid, 2,6-naphthalene dicarboxylic acid and biphenyl-4,4'-dicarboxylic acid, or a combination thereof.

The semi-crystalline semi-aromatic polyamide, obtainable from the aromatic DD salts as such, preferably has a melting temperature of at least 260° C., suitably at least 280° C. The semi-crystalline polyamide suitably has melting temperature in the range of 260-370° C., or even better the in the range from 280-350° C. This allows the polyamide to be melt-processed. Moreover, the polyamide, resulting from the combination of the aromatic DD-salt with an aliphatic DD-salt can also be melt processed and forms a homogeneous copolyamide. In fact, surprisingly, despite the fact that for the polymerization a physical mixture of salts is used and the polymerization is done in the solid-state, the process results in a block-copolymer of the aliphatic polyamide of the aliphatic DD-salt and the semi-aromatic polyamide of the aromatic DD-salt, which block-copolymer is easily converted into a random copolyamide through transamidation occurring in the melt, as observed from the melting temperature of the polymer. The semi-crystalline semi-aromatic polyamide, obtainable from the aromatic DD-salts, may also have a melting temperature at or above 370° C. This will be the case with homopolymers of XY-salts, wherein X is, for example, 1,2-ethylende diamine, 1,4-butanediamine, 1,6 hexane diamine or trans-1,4-cyclohexanediamine and Y is terephthalic acid, 2,6-naphthalene dicarboxylic acid or biphenyl-4,4'-dicarboxylic acid.

In a particular embodiment of the invention the DD-salt obtained in step (i) comprises one aromatic dicarboxylic acid (Y) and one aliphatic diamine (X), and the resulting polyamide obtained by the process is a semi-aromatic polyamide homopolymer (represented as PA-XY). Examples of suitable salts for such homopolymers include XT-salts, wherein T is terephthalic acid and X is a linear C2-C8 diamine selected from 1,2-ethylenediamine, 1,3-propanediamine, 1,4-butanediamine, 1,5-pentanediamine, and 1,6-hexanediamine. Examples of suitable polyamide homopolymers include PA-2T, PA-3T, PA-4T, PA-5T, PA-6T, PA-7T, and PA-8T. Even though such homopolymers can have a very high melting temperature, or even degrade before melting, with the process according to the invention these salts can be polymerized at a condensation reaction temperature still quite far below the melting/degradation temperature of the polymer to a very high conversion and high molecular weighs can be reached, without occurrence of side reactions resulting in gelation.

According to a second preferred aspect of the invention the dicarboxylic acid comprises an aromatic dicarboxylic acid selected from terephthalic acid, 2,6-naphthalene dicarboxylic acid and biphenyl-4,4'-dicarboxylic acid, and the liquid diamine comprises a mixture of at least two aliphatic diamines selected from C2-C10 diamines.

It has been found that including a second aliphatic diamine in the DD-salt of the invention unexpectedly accelerates the rate of solid state polymerisation in step (ii) of the process of the invention.

More preferably the DD-salt is based on an aromatic dicarboxylic acid (Y) and at least two diamines ($X_1$ and $X_2$) and optionally one or more further diamines (together referred to as $X_n$). The salts can be represented as $X_1Y/X_2Y$-salt, respectively $X_1Y/X_2Y/X_nY$-salt. The corresponding copolyamides are likewise represented as PA-$X_1Y/X_2Y$, respectively PA-$X_1Y/X_2Y/X_nY$.

The corresponding salts can be prepared by the salt-preparation step (i) by first making a liquid mixture of the at least two diamines, and then dosing the liquid mixture to the agitated powder of the dicarboxylic acid powder.

Preferably the semi-aromatic copolyamide comprises at least one aliphatic C2-C6 diamine, i.e. X1 is a C2-C6 diamine. Optionally, X2 and/or Xn comprise a diamine other than an aliphatic diamine. More preferably X1 is combined with at least another aliphatic C2-C10 diamine, i.e. X2 is an aliphatic C2-C10 diamine.

The ratio of the diamines may be varied over a wide range. For example with the molar ratio $X_1/(X_2+X_n)$ is in the range of 99/1-1/99. Above a ratio of 99/1, the (co)polyamide is rather considered to be a homopolyamide, with always some possible traces of other diamines being present. Suitably, the molar ratio $X_1/(X_2+X_n)$ is in the range 95/5-5/95, or more particular 90/10-10/90 and 75/25-25/75. Suitably, the molar amount of C2-C6 diamine is at least 50 mole % relative to the total molar amount of diamines.

Suitably, the DD-salt and the corresponding semi-crystalline semi-aromatic (co)polyamide have such a monomer combination that the melting temperature is in the range of 280-350° C., more preferably 300-340° C. These (co)polyamides exhibit good processing behaviour as well as good high temperature properties.

Examples of suitable copolyamides that can be prepared with the process according to the invention include copolymers of PA-2T, PA-3T, PA-4T, PA-5T, PA-6T, such as PA-4T/XT, PA-6T/XT, e.g. PA-4T/6T, PA-6T/5T, PA-4T/10T, PA-6T/10T, PA-6T/4T/10T, PA-6T/9T, PA-6T/7T, PA-4T/8T, PA-4T/6T/10T and PA-4T/10T, PA-6T/8T, PA4T/DACHT where DACH refers to trans-1,4-diaminocyclohexane and corresponding copolyamides wherein terephthalic acid (T) is substituted by 2,6-naphthalene dicarboxylic acid or biphenyl-4,4'-dicarboxylic acid. Herein 4 represents repeat units derived from 1,4-butanediamine, 5 represents repeat units derived from 1,5-pentanediamine, 6 represents repeat units derived from 1,6-hexanediamine, 7 represents repeat units derived from 1,7-heptane diamine, 8 represents repeat units derived from 1,8-octanediamine, 10 represents repeat units derived from 1,10-decanediamine. D represents repeat units derived from 2-methylpentamethylenediamine and 2-Me8 represent repeat units derived from 2-methyl-1,8-octanediamine.

The amount of branched aliphatic diamine in the salt preparation, if used at all, is preferably limited to 10 mole % of the diamines.

Most preferred are DD-salts based on an aromatic dicarboxylic acid selected from terephthalic acid, 2,6-naphthalene dicarboxylic acid and biphenyl-4,4'-dicarboxylic acid, and at least two aliphatic diamines selected from C4, C6 and 010 diamines.

Generally, salts of aromatic dicarboxylic acids have a higher melting temperature than their aliphatic dicarboxylic acid salt counterparts.

The DD-salt prepared from the aliphatic dicarboxylic acid, herein referred to aliphatic DD-salt, which might be prepared in combination with the DD-salt prepared from the aromatic dicarboxylic acid (referred to as aromatic DD-salt) in step (i) of the process according to the invention, suitably has a melting temperature of at least 170° C., preferably at least 180° C. or at least 190° C. Examples of such salts include XY-salts wherein X is 1,4-butane diamine, 1,5-pentanediamine, or 1,6-hexanediamine and Y is adipic acid or trans-1,4-cyclohexanedicarboxylic acid.

If copolyamides are prepared from a mixture of an aromatic DD-salt and an aliphatic DD-salt, the diamine and aliphatic dicarboxylic acid are preferably chosen such, that an aliphatic polyamide, obtainable from the aliphatic DD-salt alone would be a semi-crystalline polyamide. Suitably, such aliphatic semi-crystalline polyamide would have a melting temperature of at least 230° C., preferably at least 240° C., more preferably at least 250° C., and suitably in the range of 260-300° C. The advantage of using such aliphatic DD-salt in combination with the aromatic DD-salt, in particular with at least 50 mole % of the aromatic DD-salt, is that after the aliphatic DD-salt is converted into a prepolymer in the first condensation step (ii-a), the temperature Tc2 for the second condensation step (ii-b) can be increased after a shorter time, without sticking of the particles, meanwhile obtaining a high reaction rate and short conversion times and the overall time needed for the polymerization to obtain the polyamide of desired degree of polymerization can be shortened.

Examples of suitable copolyamides include copolymers of PA-XT with PA-X6 or PA-XCHDA, wherein X comprises a C4-C6 diamine, or a combination thereof. For example PA-4T/46, PA-4T/4CHDA, PA-6T/66, PA-6T/6CHDA and PA4T/DACH6. Herein CHDA represents repeat units derived trans-1,4-cyclohexanedicarboxulic acid.

The invention also relates to polyamides prepared by the process according to the invention, and any particular or preferred embodiments thereof. The invention in particular relates to a polyamide, obtainable by the process according to the invention, wherein the polyamide is a semi-crystalline semi-aromatic homopolyamide or a semi-crystalline semi-aromatic copolyamide.

Suitably, the polyamide has a viscosity number of at least 20 ml/g, preferably at least 35 ml/g, more preferred at least 50 ml/g, or even at least 65 ml/g.

It has been observed that the polyamide obtained by the process according to the invention have a unique physical appearance, characterised by a special morphology. The DD-salt produced in step (i) is a powder generally consisting of polycrystalline particles comprising multiple micro-crystallites. During the solid-state polymerization of the salts, either directly starting with the powder, or first granulating or pelletizing the powder under solid-state conditions, the general physical properties of the DD-salt powders, such as the basic morphology are retained largely by the polyamide powders so obtained. An example of polyamide powder particle obtained with the process according to the invention is shown in FIG. 1.

FIG. 1 shows a SEM picture of a powder particle of a semi-crystalline semi-aromatic polyamide prepared by the process according to the invention. The powder particle has the size of a few hundred micrometers. The powder particle shows a microporous structure wherein at the surface pores, cracks and many small crystallites are visible. On the left side of the picture a part of a second particle is visible.

The microcrystalline microporous structure is reflected in relatively high BET surface values for the polyamide powder while comprising relative large particles. Suitably, the polyamide powder has a BET value, measured by the method according to ISO 9277:2010 of at least 0.4 m2/g, while having at the same time a particle size distribution, measured by the method according to ISO 13320, with a d50 of at least 50 μm (micrometers). The BET value may even be in the range of 0.6-1.5 m2/g, with a d50 of at least 100 μm.

The invention is further illustrated with the following non-limiting examples and comparative experiments.

EXPERIMENTS

Raw Materials
Terephthalic acid: powder, industrial grade (particle size distribution: d10=35.8 μm; d50=127 μm d90=264 μm; span 2.36) melting temperature above 400° C.
Adipic acid: powder, industrial grade (particle size distribution: d10=102 μm; d50=349 μm; d90=758 μm; span 1.49); melting temperature 152° C.
1,4-butane diamine (1,4-diaminobutane, DAB) industrial grade; max 1 wt. % water, impurities in ppm range; melting temperature 27.5° C.
1,6-hexanediamine (Hexamethylene diamine, HMDA) industrial grade max 1 wt. % water, impurities in ppm range; melting temperature 41° C.
1,10-decane diamine; max 1 wt. % water, impurities in ppm range; Melting temperature 62° C.
sodium hypophosphite monohydrate, from Sigma Aldrich, max 1 wt. % water, impurities in ppm range.

Test Methods
End-Group Titration in DD-Salts
NH2 and CO2H content in the DD-salts were determined by potentiometric titration using a Metrohm type Titrando 808 processor with a Metrohm combi electrode using the 3 M KCl filling solution as received. 0.1 gram of salt sample were weighted into a 100 ml Glass cylindrical titration vessel, equipped with a PTFE (Teflon) coated magnetic stirring bar and dissolved into 12.5 ml water and then adding 37.5 ml ethanol. The solution was titrated for NH2 content with 0.1 N HCl in water. For the CO2H end group titration a sample solution was prepared as described above and titrated with 0.1 N NaOH in water. Blanks were run for both titrations using 50 ml of a 75 volume %/25 volume % ethanol/water solvent. The NH2 and CO2H end group content were calculated according to the following equations:

$$NH2\ content = \frac{(VHCl1 - VHCl0) \times tHCl}{a}$$

$$CO2H\ content = \frac{(VNaOH1 - VNaOH0) \times tNaOH}{a}$$

Where:
VHCl1=mL HCl titrant used for sample titration
VHCl0=mL HCl titrant used for blank titration
VNaOH1=mL NaOH titrant used for sample titration
VNaOH0=mL NaOH titrant used for blank titration
tHCl=molarity of the HCl titrant (mole/L)
tNaOH=molarity of the NaOH titrant (mole/L)
a=sample amount (g)
Viscosity Number (VN)

The viscosity number (VN) was measured according to ISO 307, fourth edition. For the measurement a pre-dried polymer sample was used, the drying of which was performed under high vacuum (i.e. less than 50 mbar) at 80° C. during 24 hrs. Determination of the viscosity number was done at a concentration of 0.5 gram of polymer in 100 ml of sulphuric acid 96.00±0.15% m/m at 25.00±0.05° C. The flow time of the solution (t) and the solvent (to) were measured using a DIN-Ubbelohde from Schott (ref. no. 53020) at 25° C. The VN is defined as $$VN = \frac{\left(\frac{t}{t_0} - 1\right)}{c} = \left(\frac{t}{t_0} - 1\right) * 200$$

wherein:
VN=viscosity number, in ml/g
t=average flow time of the sample solution, in seconds
$t_0$=average flow time of the solvent, in seconds
c=concentration, in g/ml (=0.005)
Determination of Melting Temperature (Tm) of Both the Salt as Well as the Polymer, and Melting Enthalpy (ΔHm) by DSC Method The thermal behaviour and characteristics such as melting temperature and melting enthalpy of the salts, the residual melting enthalpy of intermediate products and the melting temperature of the polymers were studied by conventional differential scanning calorimetry (DSC) applying the method according to ISO 11357-3 (2009). The measurement of residual melting enthalpy was used as an internal control for the conversion of the reaction of the salts and transformation into polyamide (pre)polymer.

For the measurements a standard heat flux Mettler DSC 823 was used and the following conditions applied. Samples of approximately 3 to 10 mg mass were weighed with a precision balance and encapsulated in (crimped) 40 μl aluminium crucibles of known mass. The aluminium crucible was sealed with a perforated aluminium crucible lid. The perforation was mechanically performed and consisted of a hole width of 50 μm. An identical empty crucible was used as a reference. Nitrogen was purged at a rate of 50 ml min-1. Heating-cooling-heating cycles with scan rates of 20° C./min, in the range of 0 to 380° C. were applied for determining the parameters that numerically characterize the thermal behaviour of the investigated materials (both salts as polymers). For the melting temperature and the residual melting enthalpy of the salts and polymers the melting peak in the first heating cycle was used.
Determination of the BET Value The BET value of the salt powders and polyamide powders was measured by the method according to ISO 9277: 2010—Determination of the specific surface area of solids by gas adsorption—BET method. The samples were analysed on a Micromeritics TriStar 3000 gas adsorption analyser. Prior to the adsorption measurements, the samples were degassed in vacuum at 100° C.

Salt Preparation

Example I: Preparation of 6T/4T Salt (61/39 Mole/Mole) in Agitated Powder Bed 61.21 g of solid terephthalic acid (0.369 mole) powder was charged into a 1.0 liter baffled flask. The flask was attached to a rotary evaporator equipped with a heated diamine dosing vessel, inertized by purging with 5 gram per hour nitrogen gas for 1 hour. The content in the flask was mixed by rotation of the flask at 50 rpm and kept under nitrogen atmosphere (5 gram per hour). The rotating flask was partially submerged in an oil bath maintained at 65° C., thereby allowing the powder to reach the same temperature. A liquid mixture of 12.67 g of 1,4-butane diamine (0.144 mole) and 26.12 g of 1,6-hexane diamine (0.225 mole) was prepared by melting and mixing the diamines at 60° C., equal to the dosing temperature of 60° C., in the dosing vessel. The liquid mixture was added drop-wise to the acid powder in 4 hours at a dosing rate of 0.42 mole %/minute under constant rotation. After completion of the dosing, the reaction mixture was stirred by rotation while keeping the flask in the oil bath at a temperature of 65° C. for another 120 minutes. Then the flask was cooled to room temperature and the salt was discharged from the flask. The salt so obtained was a powder. The results for the analytical characterization of the salt are presented in Table 1.

Example II: Preparation of 6T Salt in Agitated Powder Bed

The salt was prepared as described in Example I, except that a 2.0 liter baffled flask was used, charged with 294.18 g (1.77 mole) of terephthalic acid powder and drop wise adding a mixture of 215.82 g (1.86 mole) of 1,6-hexane diamine (HMDA) with 29.74 g of water. The temperature of the HMDA/water mixture was kept at 80° C., being the dosing temperature. Dosing rate was 1.0 g/min, (0.3875 mole % of total diamines per minute). After completion of the dosing, the temperature of the agitated powder was kept at 65° C. for 120 min while stirring. Then the flask was cooled to room temperature and the salt was discharged from the flask. The salt was obtained as a powder. The results for the analytical characterization of the salt are presented in Table 1.

Example III: Preparation of 4T Salt in Agitated Powder Bed

The salt was prepared as described in Example I, except that a 2.0 liter baffled flask was used, charged with 326.65 g (1.97 mole) of terephthalic acid powder and drop wise adding of 183.35 g (2.08 mole) of 1,4-butane diamine (DAB). The temperature of the DAB was kept at 80° C. and the temperature of the oil bath heating the baffled flask was kept at 65° C. Dosing rate was 1.0 ml/min (0.55 mole % of total diamine per minute). After completion of the dosing, the temperature of agitated powder was kept at 65° C. for 120 min while stirring. Then the flask was cooled to room temperature and the salt was discharged from the flask. The salt was obtained as a powder. The results for the analytical characterization of the salt are presented in Table 1.

Example IV: Preparation of 6T/4T Salt (64/36 Mole/Mole) in Agitated Powder Bed 228.91 g of terephthalic acid was charged into a 1 liter electrically heated cylindrical vessel equipped with a helical stirring unit with a heated top. The reactor was equipped with a dosing system connected to a heated diamine dosing vessel inertized by purging with 5 grams nitrogen gas per hour. The content in the reactor was mixed at 60 rpm and inertized by a nitrogen purge. The reactor content was heated to a temperature of 60° C. by the mantle temperature, with the top temperature kept equal to the mantle temperature. A liquid mixture of 103.26 g 1,6-hexane diamine and 44.83 g 1,4-butane diamine (64/36 mole %/mole %) was prepared by melting and mixing the diamines at 60° C. in the dosing vessel. The liquid mixture was added drop-wise through the dosing system in 5 hours under constant rotation (60 rpm) while maintaining the powder temperature of the mixture at 60° C. and maintaining a nitrogen stream of 5 grams per hour during and after addition of the diamines. After completion of the dosing of the diamines, the reaction mixture was heated from 60° C. to 150° C. in one hour and kept at that temperature for two hours while allowing the volatile components to leave the reactor. Then the reactor content was cooled to below 50° C. in two hours. The salt so obtained was a powder. The analytical results for the salt are shown in Table 1. The results are comparable to those of Example I, This illustrates that salt formation was complete in both cases, and that the staging at 150° C. for Example IV had not resulted in noticeable loss of diamine or premature reaction.

Example V: Preparation of 4T/6T/10T Salt (10/60/30 Mole/Mole/Mole with 2 Mole % DAB Excess Relative to Salt) in Agitated Powder Bed The salt was prepared as described in Example I, except that a 2.0 liter baffled flask was used, charged with 280.26 g (1.687 mole) of terephthalic acid powder and drop wise adding of liquid mixture of 117.65 g (1.012 mole) 1,6-hexane diamine, 24.87 g (0.282 mole) 1,4-butane diamine and 87.22 g (0.506 mole) 1,10-decane diamine, prepared by melting and mixing the diamines at 60° C. The temperature of the diamine mix was kept at 60° C. and the temperature of the oil bath heating the baffled flask was kept at 65° C. Dosing rate was 1.0 g/min. After completion of the dosing, the temperature of the oil bath was kept at 65° C. for 120 min while stirring. Then the flask was cooled to room temperature and the salt was discharged from the flask. The salt was obtained as a powder. The results for the analytical characterization of the salt are presented in Table 1.

Example VI: Preparation of 46/66/4T/6T Salt in Agitated Powder Bed

The salt was prepared as described in Example I, except that a 2.0 liter baffled flask was used, charged with 238.21 g (1.434 mole) of terephthalic acid powder and 38.46 g (0.263 mole) adipic acid and then drop wise adding a liquid mixture of 144.87 g (1.247 mole) 1,6-hexane diamine and 45.27 g (0.514 mole) 1,4-butane diamine, prepared by melting and mixing the diamines at 60° C. The temperature of the diamine mix was kept at 60° C. and the temperature of the oil bath heating the baffled flask was kept at 65° C. Dosing rate was 1.0 g/min. After completion of the dosing, the temperature of the oil bath was kept at 65° C. for 120 min while stirring. Then the flask was cooled to room temperature and the salt was discharged from the flask. The salt was obtained as a powder. The results for the analytical characterization of the salt are presented in Table 1. The DSC measurements showed 2 melting peaks.

Example VII: Preparation of 66/6T Salt in Agitated Powder Bed

The salt was prepared as described in Example I, except that a physical mixture of 75 g of terephthalic acid and 40.4 g of adipic acid (62/38 mole/mole %) was charged into the 1.0 liter baffled flask, to which liquid 1,6-hexane diamine (86.6 g) was added drop wise. The salt was obtained as a powder. The results for the analytical characterization of the salt are presented in Table 1. The DSC measurements showed 2 melting peaks.

Example VIII: Preparation of 4T/6T Salt with Diamine Deficiency in Agitated Powder Bed The salt was prepared as described in Example I, except that a 2.0 liter baffled flask was used, charged with 263.7 g (1.59 mole) of terephthalic acid powder and then drop wise adding a liquid mixture of 95.1 g (0.82 mole) 1,6-hexane diamine and 41.3 g (0.47 mole) 1,4-butanediamine, prepared by melting and mixing the diamines at 60° C. The temperature of the diamine mix was kept at 60° C. and the temperature of the oil bath heating the baffled flask was kept at 65° C. Dosing rate was 1.0 g/min. After completion of the dosing, the temperature of the oil bath was kept at 65° C. for 120 min while stirring. Then the flask was cooled to room temperature and the salt was discharged from the flask. The salt was obtained as a powder. The results for the analytical characterization of the salt are presented in Table 1.

Example IX: Preparation of Granulated 46/66/4T/6T Salt 2380 gram of terephthalic acid powder and 385 gram of adipic acid powder were charged into a 15 liter plough-share mixer equipped with a gas inlet, a gas outlet led through a condenser. A mixture of 453 gram of 1,4-butane diamine and 1449 gram 1,6-hexane diamine was prepared in a jacketed vessel that was maintained at a temperature of 50° C. 2.25 g of sodium hypophosphitemonohydrate was dissolved in 13 g of water and added to the diamine mixture. At the start of an experiment the mixer was charged with the solid acids and inertized with a nitrogen purge. Then, the diamine mixture was dosed to the mixer at a rate of 30 ml/min while the agitator ran at 60 RPM. After the amine mixture was dosed, the mixer was heated to 100° C. and 90 ml of additional water was added in 3 minutes. The jacket was set to 110° C. and the system was allowed to reflux for 40 minutes. The jacket was then set to 150° C. and all water and excess amines were evaporated. After opening, the mixer contained a mixture of salt granules.

Comparative Experiment A: Preparation of 6T/4T Salt (61/39 Mole/Mole) with Catalyst in Water Into a 250 cm3 stirred vessel 61.21 g of terephthalic acid (0.369 mole) and 112 g of demineralized water were added. In a second step a mix of 12.67 g of 1,4-butane diamine (0.144 mole) and 26.12 g of 1,6-hexane diamine (0.225 mole) was added. The temperature was increased to 95° C. while mixing to obtain a clear aqueous salt solution. The pH of the resulting salt solution was 7.4. Then 1.368 g of sodium hypophosphitemonohydrate (catalyst) was added to the salt solution. The resulting clear solution was concentrated in a rotary evaporator under a vacuum of 50 mbar and the resulting solid white salt was removed from the vessel and dried in a vacuum oven at 60° C. and 20 mbar to a water content less than 0.1 wt. %. The resulting salt was homogenized by crushing in a mortar, and analysed. The results of the analytical characterization are presented in Table 1.

Comparative Experiment B: Preparation of 6T/4T Salt (61/39 Mole/Mole) with Catalyst in Water Comparative Experiment A was repeated 4 times and resulting salt amounts were combined.

slightly yellowish tinted solid polymer powder. The obtained polymer was characterized by means of DSC. The first heating scan showed endothermic melting peaks characteristic to that of a polymer and at higher temperatures than the original salt peak. No traces of residual unreacted salt were detected. The DSC curve showed clearly the absence of the salt peak as recorded for the starting material. The analytical results are shown in table 2.

Comparative Experiment A-a: Polymer Synthesis from 6T/4T Salt (61/39 Mole/Mole) of Comparative Experiment A in Static Bed Reactor Example I-a was repeated except that for the salt the 6T/4T salt powder of Comparative Experiment A was used. The resulting product (yield 17.1 gram; 98.6% of theoretical yield) in the glass tube consisted of large brown coloured solid lumps. The analytical results are shown in table 2.

Example II-b: Polymer Synthesis from 6T Salt of Example II in a Stirred Reactor

The polymerization was carried out in a double walled 1 liter electrically heated metal reactor equipped with a heli-

TABLE 1

Analytical results for the salts of Examples I-IX and Comparative Example A.

| Salt sample | Composition | Process | NH2 (meq/g) | CO2H (meq/g) | ΔCO2H—NH2 (meq/g) | molar ratio NH2/CO2H | Tm (° C.) | ΔHm (J/g) |
|---|---|---|---|---|---|---|---|---|
| EX-I | 6T/4T | Powder bed | 7.32 | 7.36 | 0.04 | 0.99 | 291 | 520 |
| EX-II | 6T | Id. | 7.28 | 6.95 | −0.33 | 1.05 | 273 | 355 |
| EX-III | 4T | Id. | 8.15 | 7.72 | −0.43 | 1.06 | 286 | 531 |
| EX-IV | 6T/4T | Id. | 7.22 | 7.33 | 0.11 | 0.98 | 290 | 525 |
| EX-V | 4T/6T/10T | Id. | 7.00 | 6.62 | 0.38 | 1.06 | 280 | 474 |
| EX-VI | 46/66/4T/6T | Id. | 7.50 | 7.28 | 0.22 | 1.03 | 200 286 | 525 |
| EX-VII | 66/6T | Id | 7.45 | 7.14. | −0.31 | 1.04 | 199 275 | — |
| EX-VIII | 4T/6T a) | Id | 6.39 | 7.82 | 1.43 | 0.82 | 281 | 476 |
| EX IX | 46/66/4T/6T | Id. + b) | — | — | — | — | 204 289 | 524 |
| CE-A | 6T/4T | Solution | 7.35 | 7.42 | 0.07 | 0.99 | 282 | 520 | a) deficient in diamine;
b) followed by granulation step

Direct Solid-State Polymerization

Example I-a: Polymer Synthesis by Direct Solid-State Polymerization of 6T/4T Salt (61/39 Mole/Mole) of Example I in Static Bed Reactor A cylindrical glass tube having a 10 mm inner wall was charged with 20 g salt powder of example I and sealed at both sides with glass wool to retain the powder in the tube. The tube was placed in a glass bead packed bed. A nitrogen stream of 5 kg/hr was led through the glass bead packed bed. The powder in the tube was inertized with a nitrogen stream of 1 g/hr for 3 hours. The nitrogen stream was kept at this level during the subsequent heating and cooling steps. The powder and the surrounding glass bead packed bed were heated in 1 hour to 120° C. and subsequently in 3 hours to a temperature of 260° C., by preheating the nitrogen gas streams. The temperature was kept at 260° C. for 3 hours and then cooled to below 50° C. in 1 hour. The polymer (yield 17.28 gram, 99.6% of theoretical yield) was obtained as a cally shaped stirring unit, an inert gas inlet and an exit for the inert gas and the condensate gas to leave the reactor, and thermometers to measure the temperature of the reactor wall and the reactor content. The reactor was charged with salt powder. The salt powder was stirred and a nitrogen gas purge of 5 gram per hour was applied to inertize the reactor content. Then the reactor content was heated by heating the reactor wall applying a programmed temperature profile and monitoring the temperature of the reactor content in the powder bed, meanwhile continuing the nitrogen gas purge and stirring of the reactor content.

300 g of the salt of Example II was used. The nitrogen gas purge was set and kept at 5 gram per hour gas volume at room temperature. The reactor content was inertized during 3 hours, before starting the heating profile. The reactor content was heated from 25 to 245° C. in 180 minutes. Then the temperature was further raised to 260° C. in 90 minutes. The temperature was kept at 260° C. for 90 minutes. Then the reactor content was cooled from 260° C. to below 50° C. in 110 minutes. The resulting product (260 g, 97.0% of theoretical maximum) consisted of a slightly coloured material containing mainly powder with a slight amount of some small lumps. Analytical results are shown in table 2.

Example III-b: Polymer Synthesis from 4T Salt of Example III in a Stirred Reactor Example II-b was repeated except that for the salt 300 g of the 4T salt of Example III was used, and a temperature of 262° C. instead of 260° C. was used. The resulting product (255 g, 96.9% of theoretical yield) consisted of a slightly coloured powdery material. The analytical results are shown in table 2.

Example IV-b: Polymer Synthesis from 6T/4T Salt of Example IV in a Stirred Reactor Example III-b was repeated except that for the salt 300 g of the 6T/4T salt of Example IV was used and when reaching 262° C., a liquid mixture of 8 g 1,6-hexane diamine and 4 g 1,4-butane diamine was added over 10 minutes. Then the temperature was kept at 262° C. for another 90 minutes. Then the reactor content was cooled from 262° C. to below 50° C. in 110 minutes. Yield 258 g (98.5% of theoretical maximum yield). The resulting polyamide powder had a BET value 0.76 m2/g and a particle size distribution with a d10 of 19.7 µm, a d50 of 140 µm and a d90 of 602 µm, and a span of 2.64.

Example V-b: Polymer Synthesis from 6T/4T/10T Salt of Example V in a Stirred Reactor Example II-b was repeated except that for the salt 300 g of the 6T/4T/10T salt of Example V was used. The polymer was obtained as a powder. Yield was 262.5 g (97.4% of theoretical maximum yield).

Example VI-b: Synthesis of Polyamide 46/66/4T/6T with Salt of Example VI in a Stirred Reactor Example II-b was repeated except that for the salt 300 g of the 46/66/4T/6T salt of Example VI was used. The reactor content was heated from 25 to 215° C. in 3 hrs, kept at 215° C. for 3 hours, heated to 235° C. in 5 hrs, heated to 265° C. in 1.5 hrs, kept at 265° C. for 1 hr. Then 6 g of a mix of 2 g 1,4-butane diamine and 6 g 1,6-hexane diamine (kept in the melt at 60° C.) was added at 265° C. in 1 hr. After 2 more hours at 265° C. the reactor content was cooled from 265° C. to below 50° C. in 110 minutes. Yield was 263.0 g (95.3% of theoretical maximum yield) of a powdery material. The product had a BET value 1.7 and a particle size distribution with a d10=50.5 µm, d50=146 µm and d90=572 µm, and a span 2.30. Other analytical results are shown in table 2.

Example VII-b: Polymer Synthesis from 66/6T Salt of Example VII in a Stirred Reactor Example II-b was repeated except that for the salt 300 g of the 66/6T salt of Example VII was used and the reactor content was heated from 25 to 220° C. in 3 hrs, kept at 220° C. for 3 hours, heated to 250° C. in 5 hrs, kept at 250° C. for 5 hrs before cooling the reactor content from 250° C. to below 50° C. in 110 minutes. The resulting product (268 g, 97.1% of theoretical yield) consisted of a slightly coloured powdery material. The Analytical results are shown in table 2.

Example VIII-b: 4T/6T with 80% Diamine

Example II-b was repeated except that for the salt 300 g of the 4T/6T salt of Example VIII was used. After 1 hour at 260° C., the reaction mixture was cooled to 230° C., at which temperature a mixture of 26.6 g (0.23 mole) 1,6-hexane diamine and 11.0 g (0.13 mole) 1,4-butane diamine was dosed in 30 minutes. After the dosing the reaction mixture was heated to 240° C. and kept at that temperature for 2 hours. The reaction mixture was cooled to 230° C. and a mixture of 13.3 g (0.115 mole) 1,6-hexane diamine and 5.8 g (0.065 mole) 1,4-diaminobutane was dosed in 15 minutes. After completion of the dosing, the reaction mixture was heated again to 240° C. and kept at that temperature for 6 hours, before cooling the reactor content to below 50° C. in 2 hours. The resulting product consisted of a slightly coloured powdery material. The Analytical results are shown in table 2.

Example IX: Salt that is Used in Granulation Experiment

Three batches of salt granules of example IX were collected and charged into a 100 liter double wall tumble dryer equipped with a condenser and inert gas inlet. The content of the tumble dryer was inertized three times by alternately using a vacuum of 10 mbar absolute and a nitrogen purge to bring the dryer back to atmospheric pressure. The dryer was gradually heated from room temperature to 170° C. in 3 hours, further heated to 190° C. in 7 hours, and further heated to 260° C. in 20 hours, under nitrogen atmosphere at atmospheric pressure while keeping the tumble dryer rotating. Water evolving from the polycondensation reaction was removed via the gas phase and collected in the condenser. Sticking of granules was not observed during this heat treatment process. The analytical results are shown in table 2.

Example X: Salt Preparation and Synthesis of Polyamide 6T/4T (61/39 Mole/Mole) in a Stirred Reactor The salt preparation and polymerization was carried out in a double walled 1 liter electrically heated metal reactor equipped with a helically shaped stirring unit, an inert gas inlet and an exit for the inert gas and the condensate gas to leave the reactor, and thermometers to measure the temperature of the reactor wall and the reactor content. The reactor was charged with 183.63 g of solid terephthalic acid (1.106 mole) powder. The terephthalic acid powder powder was stirred and a nitrogen gas purge of 5 gram per hour was applied to inertize the reactor content during 3 hours. The further steps were carried out under continuous stirring of the reactor content, under constant rotation of 75 rpm, meanwhile continuing the nitrogen gas purge. The reactor content was heated by heating the reactor wall from 25 to 65° C. in 30 minutes by applying a programmed temperature profile and monitoring the temperature of the reactor content in the powder bed. A liquid mixture of 40.01 g of 1,4-butane diamine (0.454 mole) and 81.37 g of 1,6-hexane diamine (0.700 mole) was prepared by melting and mixing the diamines at 65° C., equal to the dosing temperature of the diamine mixture of 65° C., in a dosing vessel. The liquid mixture was added drop-wise to the terephthalic acid powder bed in at a dosing rate of 0.42 mole %/minute, while keeping the reactor content below 85° C. After completion of the dosing, the reaction mixture was kept at a temperature of 85° C. for another 120 minutes. Subsequently, the reactor content was heated from 85° C. to 245° C. in 180 minutes, and then from 245° C. to 260° C. in 90 minutes. The temperature was kept at 260° C. for 90 minutes. Then the reactor content was cooled from 260° C. to below 50° C. in 110 minutes. The resulting product (257 g, 97% of theoretical maximum) consisted of a slightly coloured powder material. Analytical results are shown in table 2.

Comparative Experiment CE-B-b: Polymer Synthesis from 6T/4T Salt of CE-A in a Stirred Reactor Example II-b was repeated except that for the salt 300 g of the 6T/4T salt of CE-B was used. When reaching 238° C., the experiment was stopped due to high torque development, and the reactor content was cooled to below 50° C. in 110 minutes.

TABLE 2

Analytical results for the polyamides polymers obtained from the salts of Examples I-VI and Comparative Experiment A.

| Salt sample | Com- position | Salt Process | Poly- conden- sation | Tm (° C.) | ΔHm (J/g) | VN (ml/ g) |
|---|---|---|---|---|---|---|
| EX-I-a | 6T/4T | Powder bed | Static | 330 | 103 | — |
| EX-II-b | 6T | Id. | Stirred | 373 | 137 | 74.1 |
| EX-III-b | 4T | Id. | Stirred | 426 | 50 | 24.9 |
| EX-IV-b | 6T/4T | Id. | Stirred | 334 | 132 | 81.5 |
| EX-V-b | 4T/6T/10T | Id | stirred | 334 | 102 | 65 |
| EX-VI-b | 46/66/4T/6T | Id. | Stirred | 339 a) | 96 | 80 |
| CE-A-a | 6T/4T | Solution | Static | 332 | 86 | 60 |
| CE-B-b | 6T/4T | Solution | Stirred | 331 | 30 | 28 |
| EX VII-b | 66/6T | Powder bed | Stirred | 267 355 (312$^a$) | 96 (75$^a$) | — |
| EX-VIII-b | 6T/4T | Powder bed | Stirred | 331 | 134 | 89 |
| EX-IX | 46/66/4T/6T | Granu- lation | Stirred | 333 | 107 | 69 |
| EX-X | 6T/4T | Powder bed | Stirred | 332 | 112 | 58 | a) melting temperature and melting enthalpy measured during second heating run

For the experiments according to the invention no gel was observed in the viscosity measurements. With gel is herein understood the presence of insoluble particles which, when dissolving the polymer in a typical solvent like $H_2SO_4$, would make a reliable solution viscosity measurement impossible.

Example XI: Kinetics of the Direct Solid-State Polymerization of 6T/4T Salt of Example IV 6 mg Salt Powder of Example IV was Charged in a 40 Microliter Aluminium DSC Sample Crucible without Pin and with Pre-Pierced Cover (50 Micron Hole) This sample crucible was placed on the Mettler TGA-DSC 1 robotic system. The furnace block of this instrument is cooled with a thermostate water bath system. The TGA-DSC 1 furnace of the instrument is purged with dry nitrogen gas with a flow of 50 ml/min. The nitrogen stream was kept at this level during the subsequent heating and cooling steps. The powder was heated to 150° C. at a rate of 15° C. per min. The temperature was kept at 150° C. for 5 min and subsequently heated to 260° C. at a rate of 1° C. per min. The temperature was kept at 260° C. for 4 hours and then cooled to room temperature. After 140 min from the start of the heating program, 8.1 wt % loss is observed, corresponding to a conversion of 61%.

Example XII: Kinetics of the Direct Solid-State Polymerization of 4T Salt of Example III Example XI was repeated with salt powder of example III instead of IV. After 140 min from the start of the heating program, only 2.8 wt % loss is observed, corresponding to a conversion of 20%.

The above examples XI and XII show that with the process according to the invention, the formation of a copolyamide occurs significantly faster than that of a homopolymer. The process of the invention is thus particularly suitable for the preparation of copolyamides.

The invention claimed is:

1. A process for preparing granulated particles of a semi-crystalline semi-aromatic copolyamide from diamines and a dicarboxylic acid, the process comprising the steps of:
   (i) forming a powder comprising a diamine/dicarboxylic acid salt (DD-salt) by dosing a liquid diamine mixture comprising at least two aliphatic diamines selected from C2-C10 diamines to an agitated powder comprising an aromatic dicarboxylic acid selected from the group consisting of terephthalic acid, 2,6-naphthalene dicarboxylic acid, biphenyl-4,4'-dicarboxylic acid and combinations thereof at a dosing rate of at most 4 mole % diamine per minute, relative to the molar amount of the dicarboxylic acid such that the dicarboxylic acid constitutes at least 50 mole %, relative to the total molar amount of dicarboxylic acid of the agitated powder, thereby forming the powder comprising the DD-salt in the absence of melting, and thereafter
   (ii) subjecting the powder comprising the DD-salt without intervening melting of the powder to solid-state polymerization conditions to thereby obtain the granulated particles of semi-crystalline semi-aromatic copolyamide having a microporous structure with a BET surface value of at least 0.4 $m^2/g$ as measured according to ISO 9377:2010 and a particle size distribution (d50) of at least 50 μm.

2. The process according to claim 1, which comprises subjecting the powder obtained from step (i) to a solid-state shaping process prior to conducting the solid-state polymerization according to step (ii).

3. The process according to claim 1, wherein the agitated powder further comprises an aliphatic dicarboxylic acid selected from the group consisting of adipic acid and cyclohexane dicarboxylic acid.

4. The process according to claim 1, wherein the at least two aliphatic diamines are selected from the group consisting of 1,4-butane diamine, 1,6-hexane diamine and 1,10-decane diamine.

5. The process according to claim 1, wherein step (ii) comprises the sub-steps of:
   (ii-a) condensing the DD-salt obtained in step (i) at a first condensation temperature (Tc1) at least 10° C. below the melting point of the DD-salt to produce a solid prepolymer; and
   (ii-b) conducting further condensation of the solid prepolymer resulting from step (ii-a) at a second condensation temperature (Tc2) at least 15° C. below the melting temperature of the prepolymer and the melting temperature of the resulting copolyamide to thereby obtain the granulated particles of semi-crystalline semi-aromatic copolyamide in a solid state.

6. The process according to claim 1 wherein the granulated particles of semi-crystalline semi-aromatic copolyamide have a melting temperature of at least 280° C.

7. The process according to claim 1 wherein the DD-salt has a melting temperature of at least 240° C.

8. The process according to claim 5, wherein the prepolymer has a viscosity number of at least 10 ml/g prior to step (ii-b).

9. The process according to claim 5, wherein the dicarboxylic acid comprises at least 90 mole % terephthalic acid relative to the total molar amount of dicarboxylic acid, and wherein the liquid diamine mixture comprises a C2-C10 diamine, in an amount of at least 80 mole % relative to the total molar amount of diamines.

10. The process according to claim 5, wherein step (ii-b) comprises adding supplemental diamine during the further condensation.

11. The process according to claim 1, wherein the copolyamide has a viscosity number of at least 20 ml/g, as measured in 96% sulphuric acid (0.005 g/ml) at 25° C. according to ISO 307, fourth edition.

12. The process according to claim 11, wherein the copolyamide has a viscosity number of at least 50 ml/g.

13. The process according to claim 1, wherein the aromatic dicarboxylic acid constitutes at least 80 mole %, relative to the total molar amount of dicarboxylic acid of the agitated powder.

14. The process according to claim 1, wherein the powder particles of semi-crystalline semi-aromatic copolyamide have a BET surface value of 0.6 to 1.5 $m^2/g$ and a particle size distribution (d50) of at least 100 μm.

15. A semi-crystalline semi-aromatic copolyamide powder, obtained by the process according to claim 1.

* * * * *